(12) United States Patent
Egnelöv et al.

(10) Patent No.: US 6,929,655 B2
(45) Date of Patent: Aug. 16, 2005

(54) TAMPING MECHANISM

(75) Inventors: Per Egnelöv, Uppsala (SE); Dan Åkerfeldt, Uppsala (SE); Fredrik Preinitz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 404 days.

(21) Appl. No.: 10/170,624

(22) Filed: Jun. 14, 2002

(65) Prior Publication Data

US 2003/0060846 A1 Mar. 27, 2003

Related U.S. Application Data

(60) Provisional application No. 60/298,899, filed on Jun. 19, 2001.

(30) Foreign Application Priority Data

Jun. 15, 2001 (EP) ............................. 01850106

(51) Int. Cl.$^7$ ................................. A61B 17/04
(52) U.S. Cl. ................... 606/213; 606/139; 606/144
(58) Field of Search ................ 606/139, 144, 606/213

(56) References Cited

U.S. PATENT DOCUMENTS

| 5,021,059 A | | 6/1991 | Kensey et al. |
| 5,222,974 A | * | 6/1993 | Kensey et al. ............. 606/213 |
| 5,282,827 A | | 2/1994 | Kensey et al. |
| 5,342,393 A | | 8/1994 | Stack |
| 5,350,399 A | | 9/1994 | Erlebacher et al. |
| 5,411,520 A | * | 5/1995 | Nash et al. ................. 606/213 |
| 5,441,517 A | | 8/1995 | Kensey et al. |
| 5,620,461 A | | 4/1997 | Muijs Van De Moer et al. |
| 5,707,393 A | * | 1/1998 | Kensey et al. ............. 606/213 |
| 5,935,147 A | * | 8/1999 | Kensey et al. ............. 606/213 |
| 6,007,563 A | * | 12/1999 | Nash et al. ................. 606/213 |
| 6,090,130 A | * | 7/2000 | Nash et al. ................. 606/213 |
| 6,425,911 B1 | * | 7/2002 | Akerfeldt et al. ........... 606/213 |

FOREIGN PATENT DOCUMENTS

WO    WO 00/78226 A1    12/2000

* cited by examiner

Primary Examiner—Gary Jackson
(74) Attorney, Agent, or Firm—Foley & Lardner LLP

(57) ABSTRACT

The invention relates to a loading device provided with a tamping mechanism with which two or three functional operations needed in the sealing of punctures in blood vessels can be sequentially executed in one single manual operation. In a preferred embodiment of the tamping mechanism, a cam curve (15) transforms the single manual operation of a tamping button (8) being the one end of a plunger (14) into the retraction of a pusher (5), which has been used to insert an inner seal (1) into the vessel, and, then, the advancement of a tamping tube (10), which pushes an outer seal (2) into engagement with the outer vessel wall. In the end position of the tamping button (8), a recess (23) in the plunger (14) releases a thread (3), which tamps the inner and outer seals (1, 2) together around the intermediate vessel wall, from a retainer (16), thereby completing the third operation step.

15 Claims, 7 Drawing Sheets

TAMPING MECHANISM

TECHNICAL FIELD

This invention relates to a device for sealing punctures in blood vessels, and more particularly to a loading device provided with a tamping mechanism with which three functional operations needed in the sealing of punctures in blood vessels can be sequentially executed in one single manual operation.

BACKGROUND ART

In various surgical procedures and invasive investigations, it is necessary to gain access to the blood vessels (arterial or venous). Such procedures normally involve the percutaneous puncture of the artery (or the vein) so that an introducer can be inserted into the artery. This introducer consists basically of a hollow tube through which different medical instruments, such as catheters and tracers, can be inserted into the artery. Once the operation has been completed and the medical instrument has been removed, the introducer is removed, which leaves an opening in the artery through which blood would spurt unless certain measures are taken.

The most straightforward method to stop this bleeding is by the application of direct digital pressure over the puncture site by a trained physician or other suitably trained personnel. As an alternative, the direct pressure can be applied mechanically by a large clamp provided with pressure regulating means. The direct pressure method is associated with several drawbacks, the most important one being that the pressure has to be applied for a considerable period of time. In the case of punctures into femoral arteries, the pressure may have to be applied for as long as forty-five minutes for haemostasis to occur, which results in a substantial reduction of the flow of blood through the artery. Since thrombosis is one of the major complications that can occur in the immediate post-operative period, any reduction in the flow of blood through the arterial or venous system is highly undesirably.

A more sophisticated method for stopping the bleeding is by direct mechanical sealing of the puncture in the blood vessel. The sealing device may in this case consist of a first element to be placed at the inside surface of the vessel wall, a second element to be placed at the outside surface of the vessel wall, and a clamping member that holds the first and second elements together, thereby sealing the puncture in the intermediate vessel wall. Usually the clamping member also acts as a guiding member for the second element and extends to the outside of the skin surface. Examples of such sealing devices are disclosed in U.S. Pat. Nos. 5,350,399 and 5,620,461.

With such a device, the method with which the sealing device is arranged on both sides of the vessel wall will therefore, among others, comprise the following basic steps: The first element is inserted into the blood vessel by a pushing member. The pushing member and the first element are then retracted until the first element is seated at the inside surface of the blood vessel. Then, the pushing member is pulled back, and the second element, which is guided by the guiding and clamping member, is pushed forward until the second element is seated at the outside surface of the vessel wall. The first and second elements are now being held together by the guiding and clamping member, and the intermediate vessel wall is sealed. The part of the guiding and clamping member being on the outside of the skin surface can now be released, and the guiding and clamping member is severed at the level of the skin surface.

To manually carry out these and other operation steps needed to apply the sealing device obviously require a considerable amount of manual dexterity. Assuming that the guiding and clamping member is a thread, as disclosed in, for example, U.S. Pat. No. 5,620,461, which holds the first element in engagement with the inside surface of the blood vessel and along which the second element slides into engagement with the outside surface of the blood vessel, it is obvious that the thread has to be held tightly until the first and second elements have been tamped together. Furthermore, the force needed to push to the second element into position has to be carefully adjusted, so that the force is large enough to push the second element into contact with the outside of the vessel wall. However, measures must be taken so that this force does not push the second element too hard against the vessel wall, thereby penetrating the vessel wall and enlarging the puncture hole in the vessel wall. In order to facilitate some of the operation steps mentioned above, several types of insertion tools have been developed, see, for example, U.S. Pat. Nos. 5,350,399, 5,021,059, 5,441,517, and 5,282,827. The specific design and function of these different insertion tools will, of course, depend on the designs and functions of the corresponding sealing devices.

The present invention is directed to three of the operation steps mentioned above, namely: the retraction of the pushing member, the advancement of the second element into engagement with the outside surface of the vessel wall, and the release of the guiding and clamping member. These three operation steps will be referred to as the three inventive steps, in contrast to the operation steps included in the overall sealing procedure. Thus, the three inventive steps constitute a subset of the steps normally involved in the overall sealing procedure. Throughout the present application, the pushing member will be referred to as the pusher, and the first and second elements will be referred to as the inner seal and the outer seal, respectively. The guiding and clamping member consists in this case of a thread, which runs through a hole in the centre of the outer seal and is attached to the inner seal. During the first two inventive operation steps, the thread is tightened enough to hold the inner seal securely seated against the inside surface of the vessel wall. When the outer seal is pushed forward, it slides along the thread and is guided into engagement with the outside surface of the vessel wall. Once the outer seal is positioned correctly, frictional force arising from the fact that the diameter of the hole through the centre of the outer seal is slightly less than the diameter of the thread prevents the outer seal from moving back again. The second inventive operation step is herein referred to as the tamping step. Advantageously, the third inventive operation step is executed immediately after the two preceding steps. The designs and functions of these elements as well as the different operation steps and the requirements associated with them will be described in greater detail below.

Obviously, all inventive steps should be executed as smooth and precise as possible, in order to optimise the positioning of sealing device and minimise any risks of accidentally damaging the tissue. Consequently, a need exists for a device with which these steps can be executed in safe and consistent way. The device should be easy to handle, preferably with one single manual operation, and a completely satisfactory sealing of the vessel wall should be obtained each time it is used. Preferably, the device should be provided with a safety mechanism that prevents the accidental tamping of the outer and inner seals before the seals are correctly positioned at the respective sides of the vessel wall.

SUMMARY OF THE INVENTION

The objects mentioned above are achieved with a loading device provided with a tamping mechanism according to the present invention. In a preferred embodiment, the tamping mechanism comprises a pusher, a thread, a tamping tube, a tamping button and a cam curve. As mentioned above, the pusher is used to insert the inner seal into the artery (or vein), and then the pusher and the inner seal is retracted until the inner seal is in contact with the inner surface of the arterial wall. Accordingly, this is the initial position for the first inventive step. In this position, the thread is tightened and holds the inner seal securely seated to the inner arterial wall. The tamping button is the one end of a plunger, which in the initial position is partly retracted from the proximal end of a cylindrical housing. The second end of the cylindrical housing is connected to an introducer cone, which, in turn, is connected to a feeder tube. This feeder tube has replaced the original introducer through which different medical instruments were inserted into the artery. The plunger, the pusher and the tamping tube can slide axially in the cylindrical housing, but are connected to the cam curve by pins that slides in grooves in the surface of the cam curve. The cam curve is cylindrical and can rotate in the cylindrical housing.

In the initial position, the tamping tube and the pusher are locked by the cam curve. When the tamping button is pressed, i.e. the plunger is pushed into the cylindrical housing, the cam curve will rotate, approximately 90°, and force the pusher to move backwards, and unlock the tamping tube. When the tamping button is pressed further, the plunger will leave the cam curve and instead press directly on the tamping tube, which, in turn, presses on the outer seal. In the end position, when the outer and inner seals have been tamped together, the thread, which is secured at the proximal end of the cylindrical housing, is released. Thus, the cam curve mechanism has transformed the longitudinal motion of the tamping button into three sequentially executed actions, that is: the pusher has been withdrawn from the inner seal back into the tamping tube, the tamping tube has pushed the outer seal into engagement with the outer surface of the arterial wall and tamped the outer and inner seals together, and the thread has been released.

BRIEF DESCRIPTION OF THE DRAWINGS

The loading device and the tamping mechanism are further described by way of example only, with reference to the accompanying drawings, in which.

DETAILED DESCRIPTION OF THE PREFERRED EMBODIMENT

The three inventive steps are general in the sense that they are included in a variety of sealing methods that involve a first element to be positioned at the inside surface of a vessel wall, a second element to be positioned at the outside surface of the vessel wall, and a clamping member that holds the first and second elements together. However, for illustrative purposes and to ease the understanding of the description, the three inventive operation steps will be described in conjunction with a specific system for the sealing of punctures in blood vessels. A brief description of this method will be given together with a description of the designs and functions of the different elements involved in the operation.

Figure 1:
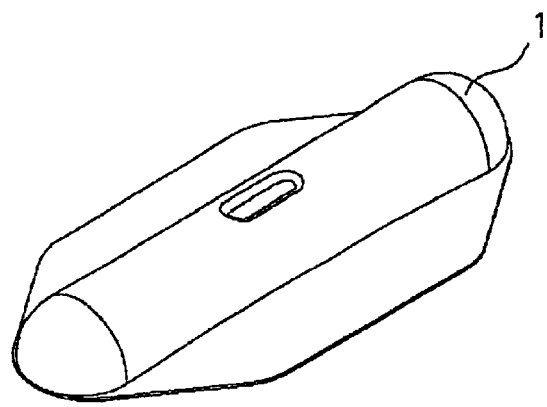
FIG. 1 is an illustration of an exemplary inner seal to be positioned into engagement with the inside surface of a blood vessel.

FIG. 1 shows an inner seal 1. In this exemplifying sealing system, the inner seal 1 is moulded of a biodegradable polymer having rubber like elasticity and which is resorbable within six months. The inner seal 1 can be folded into an introducer having a diameter of 2 mm. When the inner seal 1 is expanded, it reverts its original shape. The inner seal 1 comprises a centre beam with increased cross section thickness, which prevents the inner seal 1 from being pulled out from the blood vessel when it is seated at the inside surface of the blood vessel. A thin and flexible skirt around the centre beam provides the inner seal 1 with the pliability to adapt to and seal the vessel wall. A clamping member, in this case a thread or suture, will be drawn through the centre beam in longitudinal direction to minimise the strength reduction of the centre beam.

Figure 2:
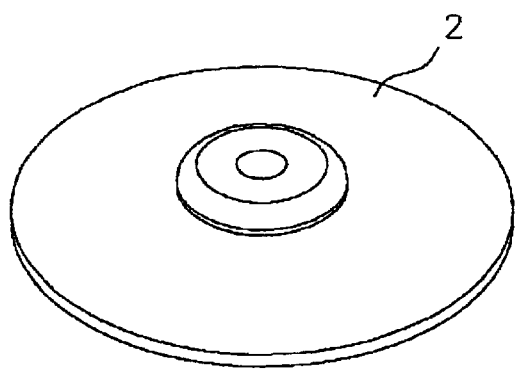
FIG. 2 is an illustration of an exemplary outer seal to be positioned into engagement with the outer surface of a blood vessel.

FIG. 2 shows an outer seal 2. In this case, the outer seal 2 is moulded of the same material as the inner seal 1. However, in other sealing systems, the inner and outer seals can be made of different materials. The outer seal 2 comprises a thicker central portion that provides the required clamping force around the thread (suture) running through a hole in the central portion. A thin and flexible skirt around the central portion provides the flexibility to adapt to the artery outside wall, and to pass through the surrounding tissue during the tamping step.

Figure 3:
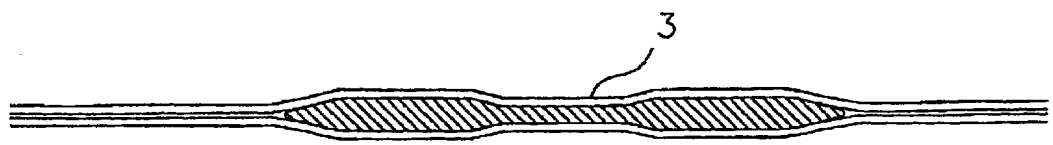
FIG. 3 is a longitudinal cross section of a thread tamping the inner and outer seals together.

FIG. 3 illustrates schematically a clamping member 3 that tamps the inner and outer seals (1, 2) together. In this case, the clamping member 3 consists of a resorbable multifilament thread, suture Polysorb™, available from US Surgical.

A moulded core pin is inserted in the centre of the braided thread 3. This core pin expands the diameter of the thread 3 at the portion where the thread 3 passes through the outer seal 2. Therefore, the outer seal 2 can slide on the thread 3 without increased friction until the outer seal 2 is in engagement with the outer vessel wall and the tamping occurs.

Figure 4:
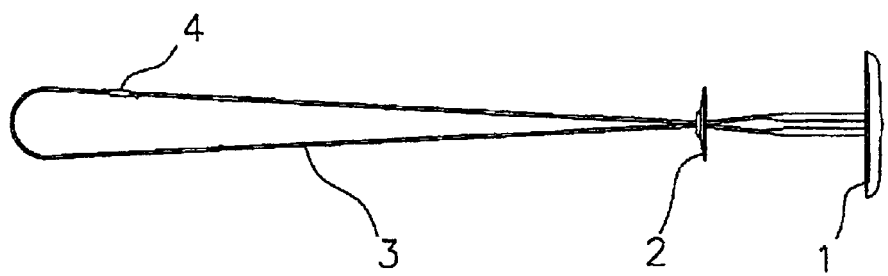
FIG. 4 is a schematic illustration of the inner and outer seals mounted together by a thread.

FIG. 4 shows the inner seal 1, the outer seal 2 and the thread 3 mounted together into a thread loop with accurate length. The thread 3 is threaded through the respective holes in the inner and outer seals (1, 2). The ends of the thread 3 are joined in a stainless steel clamp 4, which is pressed around the ends of the thread 3. Obviously, the ends of thread could be joined by other means, such as glue or tape, or could be fused together etc. Further, with other designs of the outer and inner seals, it is not necessary for the thread to take form of a loop.

Figure 5:
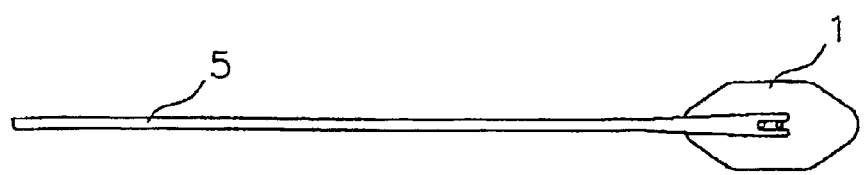
FIG. 5 is a schematic illustration of the pusher that guides the inner seal into the blood vessel.

As mentioned above, a pusher guides the inner seal 1 into the blood vessel. A pusher 5 illustrated in FIG. 5 consists of a stainless steel wire with distal end that is flattened and formed as a fork. The pusher 5 presses against the threads 3 near the inner seal 1. As seen in FIG. 5, the fork end of the pusher 5 surrounds the threads 3, and as long as the threads 3 are tightened, the pusher 5 guides the seal in all directions. Obviously, the pusher could be made of other materials, such as plastic, and, depending on the designs of the inner and outer seals as well as of the clamping member, could have some other shape, such as tubular.

Figure 6:
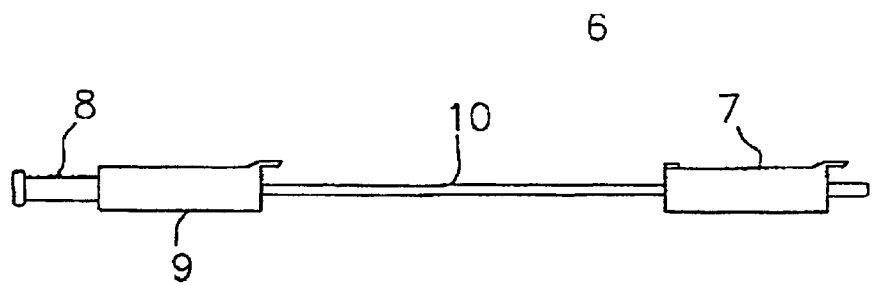
FIG. 6 is a schematic illustration of a loading device having an introducer cone and a tamping mechanism.

FIG. 6 is a schematic illustration of a loading device, generally marked with 6. The loading device 6 consists basically of two parts, an introducer cone 7 and a tamping mechanism (not shown) having a tamping button 8. The tamping mechanism is accommodated in a cylindrical housing 9, from which the tamping button 8 is partly retracted. The tamping mechanism and the introducer cone 7 is connected through an elongated tamping member 10. In the present example, the elongated tamping member 10 consists of a flexible tamping tube 10. The tamping tube 10 is attached to the tamping mechanism and can slide into the introducer cone 7. The tamping mechanism, which constitutes the basic subject of the present invention, will be described in detail below.

Figure 7:
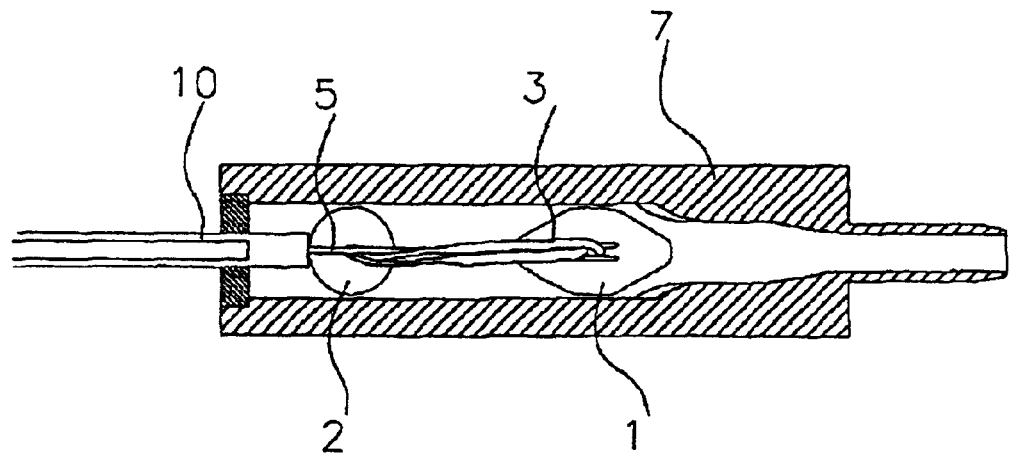
FIG. 7 is a schematic illustration of the introducer cone of FIG. 6.

FIG. 7 is a schematic illustration of the introducer cone 7 shown in FIG. 6. If the inner and outer seals (1, 2) would be permanently stored in the folded state, they would eventually adopt this shape, and would not completely resume their original shapes after deployment. In order to avoid this, the seals (1, 2) are stored unfolded in a chamber in the introducer cone 7. The introducer cone 7 is designed with an internal gradual transition from a rectangular shape to a circular shape. As the seals (1, 2) are pushed through the introducer cone 7, they will therefore be folded into a circular shape. As can be seen in FIG. 7, the thread 3 and the pusher 5 are accommodated in the tamping tube 10. With this design of the tamping member 10, the thread 3 and the pusher 5 are conveniently guided inside the tamping tube 10. However, it is also possible to use a tamping member with another design. For example, the tamping member could consist of a thin rod provided with a ring at distal end, or some other design.

Figure 8:
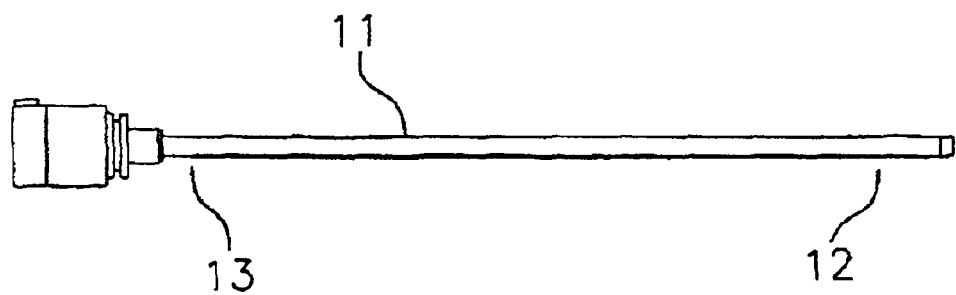
FIG. 8 is a schematic illustration of a feeder tube.
Figure 9:
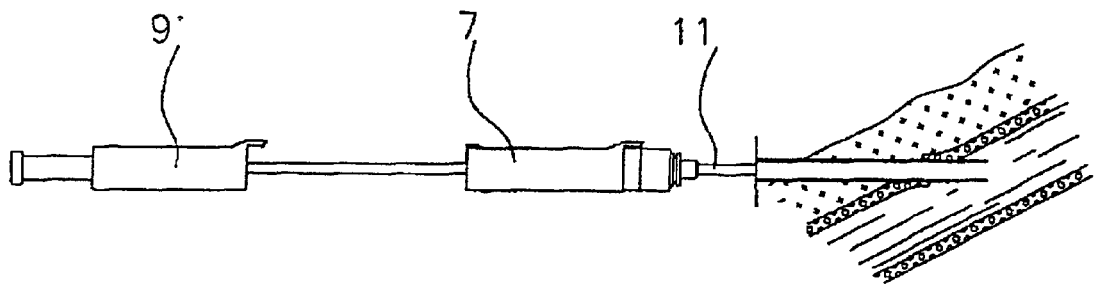
FIG. 9 illustrates the first step in the overall sealing procedure.

In the initial state, i.e. the start position for the first inventive step, the introducer cone 7 is connected to a feeder tube 11, an example of which is shown in FIG. 8. When the sealing procedure is to begin, i.e. when the medical operation in the blood vessel is completed, the original introducer is replaced with this feeder tube 11, as is illustrated in FIG. 9. Preferably, the inner seal 1 is deployed as close to the vessel wall as possible to minimise the risk associated with the manipulation of the inner seal 1 inside the blood vessel. For that purpose, the feeder tube 11 illustrated in FIG. 8 is provided with small back flow channel in the tube wall, with a distal inlet 12 approximately 1 cm from the tip and a proximal outlet 13. By observing the blood drip from the channel outlet 13 it is possible to position the tip of the feeder tube 11 a suitable distance—in this case 1 cm—into the blood vessel. As is known in the art, the positioning of the feeder tube 11 can accomplished with various different methods. Further, the feeder tube 11 shown in FIG. 8 is provided with a snap fit mechanism for snap fit connection to the introducer cone 7, but other types of connection mechanisms, such as a bayonet coupling, are possible.

As described above, the loading device 6 comprises also a tamping mechanism. This tamping mechanism, the function of which is the essential part of the present invention, will be thoroughly described below. However, in order to facilitate the understanding of the tamping mechanism and its functions, the steps usually involved in the overall sealing procedure—i.e. not only the three inventive steps—will first be described very briefly.

In FIG. 9 the original introducer has been replaced with the feeder tube 11. A person skilled in the art would recognize how this procedure is accomplished. For clarity of the illustration, the right side of FIG. 9 (as well as the right side of FIGS. 10 to 14), i.e. the distal end of the feeder tube 11, has been enlarged in comparison with the left side of FIG. 9 (and FIGS. 10–14), i.e. the proximal end of the feeder tube 11. In this first step of the overall sealing procedure, the introducer cone 7 is inserted into the feeder tube 11 until the introducer cone 7 and the feeder tube 11 snap together by means of the snap fit mechanism.

Figure 10:
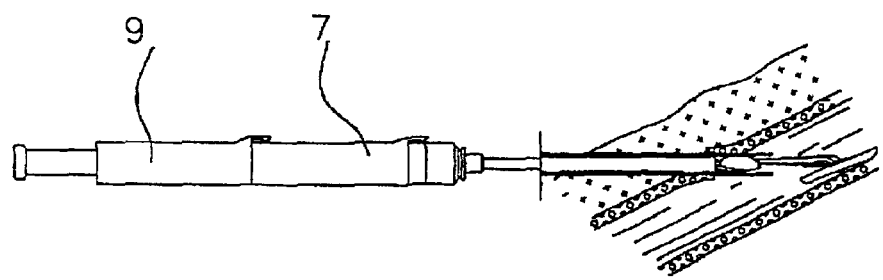
FIG. 10 illustrates the second step in the overall sealing procedure.

The second step in the overall sealing procedure is illustrated in FIG. 10, where the tamping mechanism being accommodated in the cylindrical housing 9 is pushed into the introducer cone 7 until the cylindrical housing 9 and the introducer cone 7 snap together. This step deploys the inner seal 1 into the blood vessel.

Figure 11:
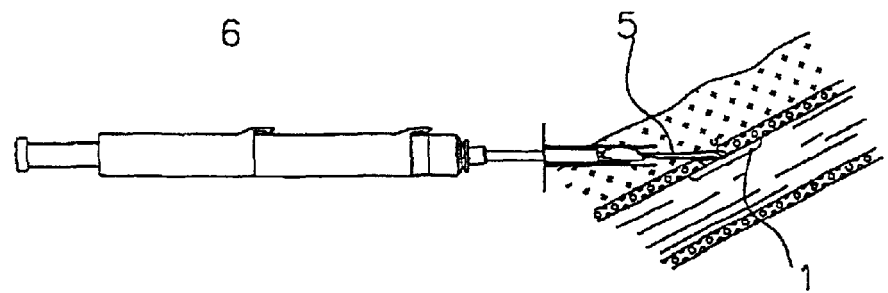
FIG. 11 illustrates the third step in the overall sealing procedure.

In FIG. 11 the third step in the overall sealing procedure is illustrated. In this step, the loading device 6 is pulled back until the inner seal 1 is seated to the inner vessel wall. The loading device 6 is held steadily and the thread 3 is tightened.

Figure 12:
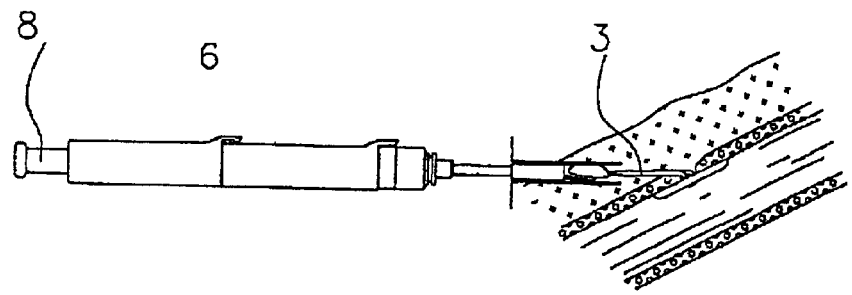
FIG. 12 illustrates the first inventive step.

The fourth step in the overall sealing procedure is illustrated in FIG. 12. This fourth step in the overall sealing procedure constitutes at the same time the first step of the three inventive steps. In the first inventive step, the pusher 5 is retracted from the inner seal 1 into the tamping tube 10. The inner seal 1 is now held in position by the thread 3.

Figure 13:
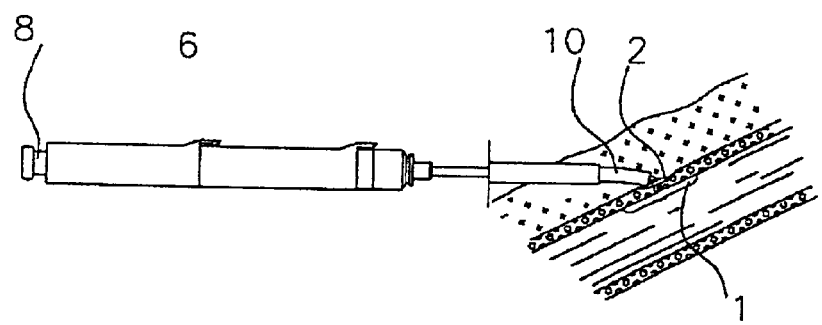
FIG. 13 illustrates the second inventive step.

FIG. 13 illustrates the fifth step in the overall sealing procedure, i.e. the second inventive step. In the second inventive step, the tamping tube 10 is pushed forward and tamps the inner seal 1 and the outer seal 2 together.

Figure 14:
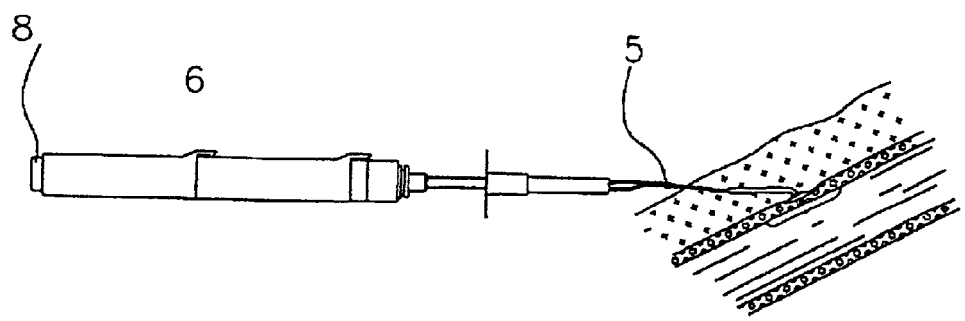
FIG. 14 illustrates the third inventive step.

FIG. 14 illustrates the sixth step in the overall sealing procedure, i.e. the third and last inventive step. In the third inventive step, the thread loop shown in FIG. 4 is released from the loading device 6, and the loading device 6 can be removed, leaving only the thread 3 in the puncture channel.

As can be seen in FIGS. 12, 13 and 14, the position for the tamping button 8 of the loading device 6 is gradually changing from a fully retracted state to a completely compressed state during the three inventive steps. In other words, the single manual operation of pressing down the tamping button 8 actuates and accomplishes the three inventive steps. Clearly, the functions associated with the inventive steps have to be executed sequentially; i.e. the first function comprising the retraction of the pusher 5 must be completed before the beginning of the second function comprising the advancement of the tamping tube 10 into engagement with the outer vessel wall. The second function must, in turn, be completed before the beginning of the third function comprising the release of the thread 3 from the loading device 6. The tamping mechanism according to the present invention satisfies these requirements.

In some sealing systems it may be enough that the three inventive steps are executed in an essentially sequential order. In this case, some degree of overlap is allowed between some of the three inventive steps, i.e. a subsequent step may start before the preceding step has been fully completed.

From the above it should be apparent that tamping mechanism should be able to transform the movement of the tamping button 8 in the forward direction into a movement of the pusher 5 in the backward, or retracting, direction. Here the forward direction is the direction of the tamping button 8 that pushes the tamping member 10 forward into engagement with the outer vessel wall. Since the tamping member 10 in this case consists of a flexible tamping tube 10, it is not necessary to mount the tamping mechanism and the introducer cone 7 in an aligned relation, although it seems practical. Also in such a case, when the tamping tube 10 and the tamping button 8 is not aligned, a direction of motion for the tamping button 8 that pushes the tamping tube 10 forward would therefore also be regarded as the forward direction.

Figure 15:
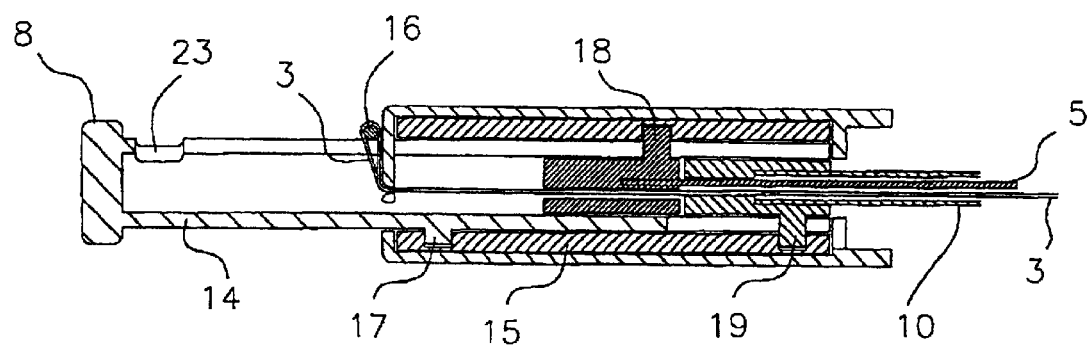
FIG. 15 is a sectional view of a preferred embodiment of the tamping mechanism according to the present invention.

A preferred embodiment of the tamping mechanism according to the present invention is illustrated in FIG. 15. The tamping mechanism comprises the pusher 5, the thread 3, the tamping tube 10 and the tamping button 8 as well as a plunger 14 and a cam curve 15. As seen in FIG. 15, the tamping button 8 is the one end of the plunger 14. However, in some other embodiment of the sealing device, the tamping button could be operatively connected to the plunger by means of some force transmitting means.

In the initial position shown in FIG. 15, the plunger 14 is partly retracted from the cylindrical housing 9. As mention in connection to FIG. 4, the thread 3 is formed into a loop. This loop is fastened around a retainer 16 mounted at the proximal end of the cylindrical housing 9. The cam curve 15 is cylindrical and can rotate in the cylindrical housing 9. The plunger 14, the pusher 5 and the tamping tube 10 can slide axially in the cylindrical housing 9, but they are connected to the cam curve 15 by pins (17, 18, 19) that slide in grooves (20, 21, 22) in the surface of the cam curve 15. In the initial position, the tamping tube 10 and the pusher 5 are locked by the cam curve 15. When the tamping button 8 is pressed forward towards the cylindrical housing 9, the cam curve 15 will rotate, approximately 90°, and force the pusher 5 to move backwards, and unlock the tamping tube 10. When the tamping button 8 is pressing the plunger 14 further into the cylindrical housing 9, the plunger 14 will leave the cam curve 15 and instead press directly against the tamping tube 10.

Figure 16:
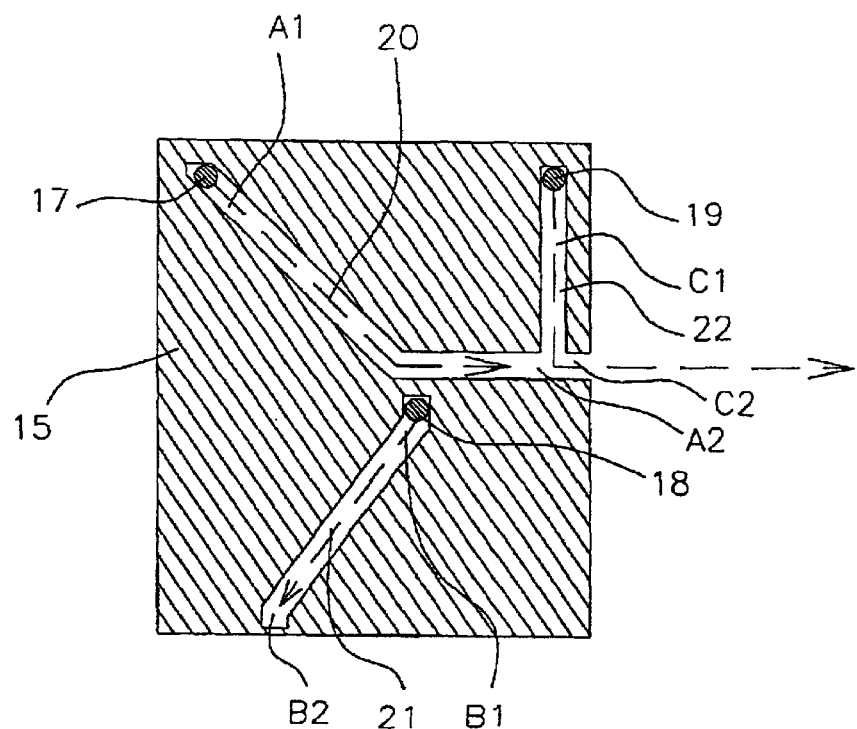
FIG. 16 illustrates one embodiment of the cam curve included in the tamping mechanism of FIG. 15.

The function of the cam curve 15 is more easily understood from the illustration shown in FIG. 16, where one embodiment of the cam curve 15 is shown in an outspread state. A pin 17, which can run in a groove 20 in the cam curve 15, connects the tamping button 8 to the cam curve 15, a pin 18, which can run in a groove 21, connects the pusher 5 to the cam curve 15, and a pin 19, which can run in a groove 22, connects the tamping tube 10 to the cam curve 15. As the tamping button 8 is pressing the plunger 14 a first distance into the cylindrical housing, the pin 17 connecting the tamping button 8 to the cam curve 15 is moving from the position marked with A1 in FIG. 16 to the position marked with A2. During this first motion the pin 18 connecting the pusher 5 to the cam curve 15 has moved from the position marked with B1 to the position marked with B2. This means that the pusher 5 has been withdrawn into the cylindrical housing 9, i.e. the first inventive step has been completed. While the pin 17 has moved from position A1 to position A2, the pin 19 connecting the tamping tube 10 to the cam curve 15 has moved from the position marked with C1 to the position marked with C2. Since the tamping tube groove 22 is perpendicular to the direction of motion of the plunger 14, the first motion of the plunger 14 does not move the tamping tube 19 closer to the outer vessel wall. As the tamping button 8 is pressed further towards the cylindrical housing 9, the plunger 14 will leave the cam curve 15 and instead press directly against the tamping tube 10, which, in turn, pushes the outer seal 2 into engagement with the outer vessel wall, thereby tamping the outer and inner seals (1, 2) together. When the tamping button 8 has been pressed into its end position, the second inventive step is completed. In this end position, the retainer 16 will fall down into a recess 23 (see FIG. 15) in the plunger 14 adjacent to the tamping button 8, which releases the thread 3 from the retainer 16, thereby completing the third inventive step.

Note that FIG. 16 is merely for illustrative purposes. As mentioned above, the cam curve 15 is preferably cylindrical and rotates in the cylindrical housing 9. In the outspread state shown in FIG. 16, the corresponding motion of the cam curve 15 would therefore be in the upward direction. However, to actually let the cam curve 15 have the outspread shape shown in FIG. 16 would also work in practise, although this outspread shape might occupy more space than a cylindrical shape. Obviously, if the cam curve is not cylindrical, there is no particular reason for the housing 9 to be cylindrical.

As should be apparent from the above, the last inventive step follows immediately after the second inventive step, which is an advantage since this minimises the risk of damaging the vessel wall or other tissue. Depending on the specific design and mounting of the retainer and/or the thread, the recess 23 in the plunger 14 may be replaced with some other retainer actuating means 23. If, for some reasons, the user wants to release the thread 3 by a separate manual operation, the retainer actuating means 23 could, of course, be omitted. In this case, the tamping mechanism executes only two of the three inventive steps.

As stated above, the division of the tamping procedure into three sequentially executed actions is necessary for the correct and safe sealing of the puncture in the vessel wall. However, it should be recognised that from a user point of view this division is rather uninteresting since he/she just presses the tamping button into the cylindrical housing by one simple and steady motion.

Figure 17:
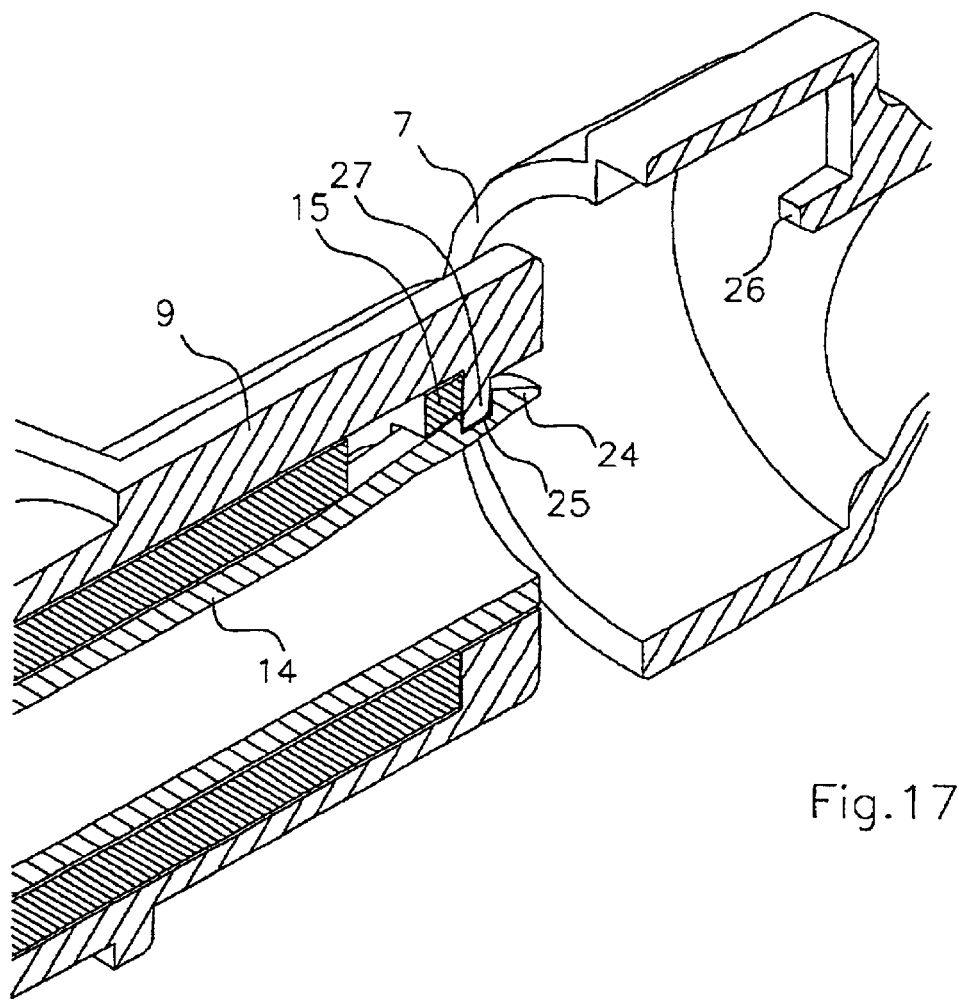
FIG. 17 shows a safety mechanism for the loading device of FIG. 6.

As mentioned above, it is preferred to provide the loading device 6 with a safety mechanism that prevents the accidental tamping of the outer and inner seals (1, 2) before the seals (1, 2) are correctly positioned at the respective sides of the vessel wall. The specific design and function of such a safety mechanism will, of course, depend on the specific design and function of the corresponding tamping mechanism. Further, the safety mechanism could be a mechanism that is manually actuated in a separate operation, or the safety mechanism could be an automatic mechanism, which means that the release of the tamping mechanism is done automatically in one of the steps included in the overall sealing procedure without any separate actions by the user. In FIG. 17 one embodiment of such a safety mechanism is illustrated. The safety mechanism comprises a flexible catch 24 provided with a groove 25, and a pin 26. The catch 24 constitutes in this embodiment a part of the plunger 14 and is mounted in operative engagement with the cam curve 15. The pin 26 is mounted inside the introducer cone 7. In FIG. 17, the safety mechanism is shown before the introducer cone 7 and the cylindrical housing 9 are snapped together, i.e. before the second step in the overall sealing procedure. As seen in FIG. 17, the catch 24 is tilted slightly upwards and is thereby preventing the cam curve 15 from rotating. At the same time, the groove 25 being in engagement with a projection 27 from the inside surface of the cylindrical housing (9) prevents the plunger 14 from sliding into the cylindrical housing 9. When the second step in the overall sealing procedure is completed, i.e. when the cylindrical housing 9 and the introducer cone 7 have been snapped together, the flexible catch 24 is pressed down by the pin 26, thereby releasing the plunger 14 and the cam curve 15. Obviously, there are other means to accomplish this safety function.

Figure 18:
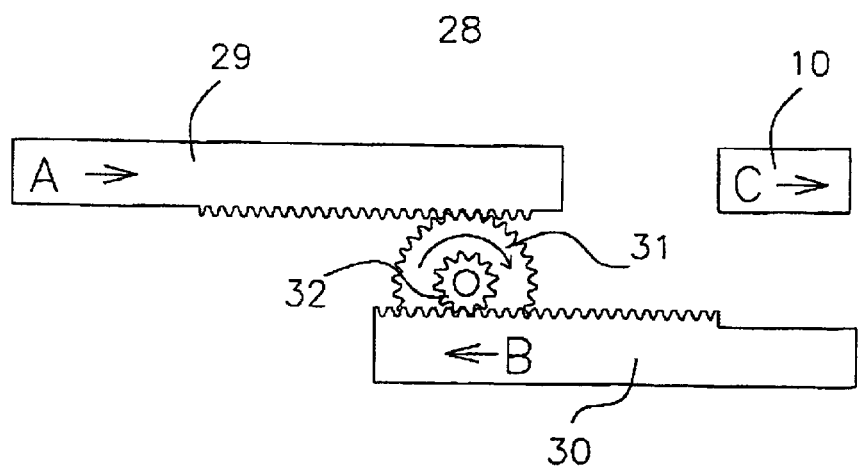
FIG. 18 is schematic illustration of an alternative embodiment of the tamping mechanism according to the invention.

While the cam curve according to the present invention is a practical and preferred way to transform the forward motion of the tamping button into the three sequentially executed inventive steps, it exists a variety of other means to accomplish this. FIG. 18 illustrates schematically an alternative embodiment of the motion transforming means according to the invention. In this case, the cam curve 15 has been replaced with a gear mechanism, generally marked with 28. The gear mechanism 28 comprises a partly cogged plunger 29, a partly cogged pusher 30, an elongated tamping member 10, and two gear wheels (31, 32) connected to each other. The cogs of the plunger 29 are initially in operative engagement with the gear wheel 31 having the larger diameter. The cogs of the pusher 30 are initially in operative engagement with the gear wheel 32 having the smaller diameter. As the cogged plunger 29 is pressed forward, as indicated by the arrow A, the two gear wheels (31, 32) will rotate in the clockwise direction, as illustrated in FIG. 18. The gear wheel 32 will therefore move the cogged pusher 30 backwards, as indicated by the arrow B, thereby executing the first inventive step. When the plunger 29 is pressed further forward, there are no more cogs in operative engagement with the gear wheel 31, and the plunger 29 presses directly against the tamping member 10, which moves forward, as indicated by the arrow C, thereby executing the second inventive step. By varying the relative diameters of the two gear wheels (31, 32), the first inventive step can be completely executed before the beginning of the second inventive step. Obviously, it is also possible to adjust the overlap between the first and second inventive steps by adjusting the distance between the cogged plunger (29) and the tamping member (10). In this case, it is also possible to have two gear wheels with the same diameter, which, in practise, means that only one gear wheel is used.

Although the present invention has been described with reference to specific embodiments, also shown in the appended drawings, it will be apparent for those skilled in the art that many variations and modifications can be done within the scope of the invention as described in the specification and defined in the following claims.

What is claimed is:

1. Tamping mechanism for the sealing of a percutaneous puncture in the wall of a vessel, which sealing procedure comprises the steps of inserting an inner seal (1) into the vessel by a pusher (5; 30), pushing an outer seal (2) into engagement with the outer vessel wall, and tamping the inner seal (1) and the outer seal (2) together around the intermediate vessel wall by a clamping member (3), characterized in that the tamping mechanism, which is accommodated in a housing (9), comprises the pusher (5; 30), the clamping member (3), a tamping button (8) being operatively connected to a plunger (14; 29), an elongated tamping member (10) being able to transmit the pressure force from the plunger (14; 29) to the outer seal (2), and a motion transforming assembly (15; 28), which transforms a single manual operation of the tamping button (8) in the forward direction into two actions, the first action comprising the retraction of the pusher (5; 30), and the second action comprising the advancement of the outer seal (2) into engagement with the outer vessel wall.

2. Tamping mechanism according to claim 1, characterized in that said two actions are executed in an essentially sequential order.

3. Tamping mechanism according to claim 1, characterized in that the clamping member (3) is a thread, which runs through an opening in the outer seal (2) and the distal end of which is fastened to the inner seal (1), the proximal end of the thread (3) being tightened and secured by a retainer (16) mounted on the housing (9).

4. Tamping mechanism according to claim 3, characterized in that the retainer (16) is actuated by a retainer actuating assembly (23) when the tamping button (8) enters its end position, thereby releasing the thread (3) from the retainer (16).

5. Tamping mechanism according to claim 4, characterized in that the retainer actuating assembly (23) is a recess in the plunger (14; 28), into which recess (23) the retainer (16) falls when the tamping button (8) enters its end position, thereby releasing the thread (3) from the retainer (16).

6. Tamping mechanism according to claim 4, characterized in that the release of the thread (3) constitutes an additional, third, action.

7. Tamping mechanism according to claim 6, characterized in that said three actions are executed in an essentially sequential order.

8. Tamping mechanism according to claim 1, characterized in that the motion transforming assembly (15) comprises a cam curve (15), which is movable in the housing (9) and to which the pusher (5), the plunger (14) and the tamping member (10) are connected by a respective pin (17, 18, 19) that can slide in a respective groove (20, 21, 22) provided in the surface of the cam curve (15), which grooves (20, 21, 22) are arranged so that, when the tamping button (8) is pressed and the plunger (14) is moving a first distance into the housing (9), the cam curve (15) will move and force the pusher (5) to move backwards, and when the plunger (14) is pressed further into the housing (9), the plunger (14) will press directly against the tamping member (10).

9. Tamping mechanism according to claim 8, characterized in that the cam curve (15) is cylindrical and rotatable in the housing (9).

10. Tamping mechanism according to claim 9, characterized in that the tamping mechanism is provided with a safety mechanism comprising a pin (26), which is mounted at the proximal end of an introducer cone (7), and a flexible catch (24), which is provided with a groove (25) and mounted at the distal end of the plunger (14), so that, before the introducer cone (7) and the housing (9) have been snapped together, the flexible catch (24) is tilted outwards and prevents the cam curve (15) from rotating around the plunger (14) in the housing (9) and, at the same time, the groove (25) in the flexible catch (24), which is in engagement with a projection (27) from the inner surface of the housing (9), prevents the plunger (14) from sliding into the housing (9), and when the introducer cone (7) and the housing (9) have been snapped together, the flexible catch (24) is pressed down by the pin (26), thereby releasing the plunger (14) and the cam curve (15).

11. Tamping mechanism according to claim 8, characterized in that, when the cam curve (15) is outspread to a sheet, the groove (20) for the plunger pin (17) and the groove (21) for the pusher pin (18) take the general form of the letter Y, with the groove (22) for the tamping member pin (19) being provided as an extra groove (22) near the bottom end of the base of the letter Y, and the groove (21) for the pusher pin (18) being the upper branch of the letter Y being on the opposite side of the base of the letter Y as the extra groove (22); so that, in the initial position, the plunger pin (17) is in the upper end position, the pusher pin (18) is near the base of the letter Y, and the tamping member pin (19) is in the outer end position in the extra groove (22), which is perpendicular and open to the groove (20) for the pusher pin (18).

12. Tamping mechanism according to claim 1, characterized in that the motion transforming assembly (28) comprises a gear mechanism (28), which comprises the tamping member (10), a partly cogged plunger (29) in engagement with a first gear wheel (31) being connected to a second gear wheel (32), and a partly cogged pusher (30) in engagement with the second gear wheel (32); so that, when the cogged plunger (29) is pushed in the forward direction and rotates the first and second gear wheels (31, 32), the second gear wheel (32) moves the cogged pusher (30) backwards, thereby executing the first of said actions, and when the cogged plunger (29) is pushed further, the first gear wheel (31) comes out of engagement with the cogged plunger (29) by entering the portion of the partly cogged plunger (29) that has no cogs and the cogged plunger (29) presses directly against the tamping member (10), thereby executing the second of said actions.

13. Tamping mechanism according to claim 12, characterized in that the first gear wheel (31) and the second gear wheel (32) have different diameters.

14. Tamping mechanism according to claim 12, characterized in that the first gear wheel (31) and the second gear wheel (32) have the same diameter, thereby, in practice, constituting one single gear wheel.

15. Tamping mechanism according to claim 1, further comprising a safety mechanism that prevents accidental tamping of the inner and outer seals (1, 2).

* * * * *